United States Patent
Kim et al.

(10) Patent No.: US 7,144,919 B1
(45) Date of Patent: Dec. 5, 2006

(54) POLYOXYETHYLENE-POLYOXYPROPYLENE VITAMIN E AND PROCESS FOR PREPARATION THEREOF

(76) Inventors: Youngdae Kim, 3-1407, Sunkyung Apartment #506, Taechi-dong, Kangnam-ku, Seoul 135-280 (KR);
Keunja Park, 3-1407, Sunkyung Apartment #506, Taechi-dong, Kangnam-ku, Seoul 135-280 (KR);
Jungsoo Kim, 3-1407, Sunkyung Apartment #506, Taechi-dong, Kangnam-ku, Seoul 135-280 (KR);
Jisoo Kim, 3-1407, Sunkyung Apartment #506, Taechi-dong, Kangnam-ku, Seoul 135-280 (KR)

( * ) Notice: Subject to any disclaimer, the term of this patent is extended or adjusted under 35 U.S.C. 154(b) by 539 days.

(21) Appl. No.: 10/362,160

(22) PCT Filed: Aug. 23, 2000

(86) PCT No.: PCT/KR00/00948

§ 371 (c)(1),
(2), (4) Date: Feb. 21, 2003

(87) PCT Pub. No.: WO02/20508

PCT Pub. Date: Mar. 14, 2002

(51) Int. Cl.
*A61K 31/355* (2006.01)
*C07D 309/93* (2006.01)

(52) U.S. Cl. ............... 514/458; 514/844; 514/847; 514/886; 514/937; 514/941; 514/946; 549/407

(58) Field of Classification Search ............... 549/408; 514/458, 844, 847, 886, 937, 941, 946; 424/400
See application file for complete search history.

(56) References Cited

U.S. PATENT DOCUMENTS

| | | | |
|---|---|---|---|
| 5,235,073 A | 8/1993 | Kim et al. | 549/408 |
| 5,441,725 A | 8/1995 | Kim et al. | 424/59 |
| 5,869,703 A * | 2/1999 | Kim et al. | 549/408 |
| 6,355,811 B1 * | 3/2002 | Kim et al. | 540/408 |
| 6,417,223 B1 * | 7/2002 | Sanders et al. | 549/408 |

* cited by examiner

*Primary Examiner*—Thomas McKenzie
*Assistant Examiner*—Raymond Covington
(74) *Attorney, Agent, or Firm*—Nath & Associates PLLC; Gary M. Nath (57) ABSTRACT

The present invention relates to polyoxyethylene-polyoxypropylene (POE-POP) vitamin E, which is prepared from vitamin E by polyethoxylation and polypropoxylation, and a method for preparing the same. The POE-POP vitamin E has a high surface activity and an excellent safety for the skin, so that the POE-POP vitamin E can be advantageously used in the cosmetic industry, the food industry and the medical industry.

8 Claims, 5 Drawing Sheets

A: POE(30EO)-POP(20PO) Vitamine E
B: POE(10EO) Vitamine E
C: POE(20EO) Sorbitan Stearate/ Sorbitan Sesquioleate=3/

FIG. 9

A: POE(5EO)-POP(20PO) Vitamine E
B: POP(5EO) Vitamine E
C: Sorbitan Sesquioleate /POE(20) Sorbitan Stearate=9/1

US 7,144,919 B1

POLYOXYETHYLENE-POLYOXYPROPYLENE VITAMIN E AND PROCESS FOR PREPARATION THEREOF

TECHNICAL FIELD

The present invention relates to novel polyoxyethylene-polyoxypropylene (hereinafter referred to as "POE-POP") vitamin E and a method for preparing the same. More particularly, the present invention relates to amphipathic POE-POP vitamin E which is of high surface activity and safe for use on the skin with skin soothing and antioxidant functions, and a method for preparing the same. Also, the present invention is concerned with the uses of such novel POE-POP vitamin E.

BACKGROUND ART

Surfactants, which are amphipathic in essence, have useful applications in a broad spectrum of industries, including medicines, foods, cosmetics, etc, with classification into dispersants, emusifiers, solubilizers, foaming agents, anti-foaming agents, polishing agents, lubricants, surface-treating agents, wetting agents and so forth, depending on function and purpose. Because of their thermodynamic instability, surfactant products are manufactured by various methods associated with kinds and amounts of surfactants, solvents, viscosity, stirring, temperature, etc. Surfactants find numerous applications in various industries: one of the most active fields of research into surfactants may be found in the production of emulsion products. Nonionic surfactants in current use in the food, medicine and cosmetic industries may be representatively exemplified by POE sorbitan fatty acid esters, sorbitan fatty acid esters, glyceryl fatty acid esters, POE fatty alcohol ethers, POE alkylphenol, and POE-POP-POE copolymers, which are extensively used owing to their excellent surface activity.

Usually, in practice, the stability of emulsion products made of surfactants is obtained by using in HLB values of surfactants, volume ratio of inner phase to outer phase, and viscosity. However, it is difficult to keep emulsion products of very low viscosity stable for a long period of time. Particularly, it is hard to stabilize, for a long period of time at high temperature (37–40° C.), the products which are produced using such conventional surfactants at low concentrations by usual processes, i.e., with a homogenizer. In fact, there is a strong demand for emulsion products that are highly stable under various conditions, and active research has been directed to the development of surfactants which allow emulsion products of high stability to be produced by usual processes.

As a rule, surfactants are adsorbed to the interfaces or surfaces of aqueous solutions to significantly reduce the interfacial tension or surface tension of the solutions. The performance and functions of surfactants result not from individual surfactant molecules, but from the assembly of surfactant molecules. In water, surfactant aggregations unite themselves through physical interaction, forming a monolayer or other various structures, examples of which include micelles, vesicles, liposomes, bilayers, and multilayers. In aqueous solutions of sufficient concentrations, most surfactants ultimately form uniform single phases known as mesophases or liquid crystals. If a surfactant has a molecular structure more favorable for the formation of liquid crystals in a uniform single phase, the molecules of the surfactant can be more orderly arranged and thus, form a more stable structure at a less concentration.

It is very interesting that many biosystems show liquid crystal properties. Mesophase represented for liquid crystal is an intermediate state of liquid and solid, and is found in various sites of the body: sterols or lipid analogs may be in mesophase (Encyclopedia of Chemical Technology, $3^{rd}$, Ed. Vol. 14, pp 395–427, Wiley-Interscience, 1984, U.S.A.). Also, liquid crystals seem to play an important role in the structure and biochemical functions of cells. Acting as surfactants in the body, lipids have influence on the physiological functions of organs and tissues. It is no exaggeration to say that life cannot be maintained without surfactants. Cell membranes are composed mainly of amphiphiles among which phospholipids are prevalent. Amphiphiles organize themselves into bilayer structures in which the molecules are closely packed in such a way that hydrophilic moieties are directed outward while hydrophobic moieties are arranged inwardly, constituting the inner phase without contacting with the aqueous environment. Existing as the outermost layer of the human skin, the stratum corneum is made up of cells. The stratum corneum is physiologically active, but is considered to be a dead material because its cell nuclei are atrophied. However, the stratum corneum, which deserves to be an important example of liquid crystals, acts as a barrier, consisting of the lipids which are responsible for the transportation of water, chemicals, biologically active materials, etc. In the body, the liquid crystals are very important in physiological and medical aspects. It is difficult molecules to diffuse across liquid crystal membranes, but to do rapidly and anisotropically along liquid crystal layers as in a liquid phase. In consequence, liquid crystal phases are closely associated with physiological activity.

Studies into surfactant structures revealed that hydrophobic interactions are the major driving force for the self-assembly or aggregation of amphipathic surfactants in aqueous solutions and thus, the structural characteristics of surfactants are primarily determined by the hydrophobic alkyl region of the surfactant molecules. Based on this fact, the present inventors disclosed that vitamin E is well inserted into the ordered, dense lipid bilayers of cell membranes, acting to protect against the oxidation of the cell membranes, and is advantageous to the formation of liquid crystals owing to its structure consisting of a hard, flat chromane ring and a flexible phytyl group (Young-Dae, Kim and Byung-Jo, Ha, Cosmetics & Toiletries, 108, April, 63–78 (1993)).

In addition, with knowledge of the structural and functional properties of vitamin E, the present inventors also formulated the hypothesis that vitamin E could play an efficient role as a hydrophobic group if it is applied to surfactants, and finally invented POE vitamin E having surfactant activity as well as skin-soothing action and moisture retention and anti-oxidative effects to protect cells from harmful active oxygen by adding ethylene oxide (EO) to vitamin E (Korean Pat. No. 083024; U.S. Pat. No. 5,235,073; Japanese Pat. Appl'n No. Hei 4-10362).

By virtue of its structural characteristics, the POE vitamin E is well absorbed into the interface of aqueous and lipid phases, showing excellent surface activity. However, since the POE vitamin E is of low hydrophobicity owing to its relatively small hydrophobic alkyl tail and the presence of oxygen atom (O) at an internal position of the chromane ring, it can have constant HLB values with the use of a small hydrophobic moiety (Young-Dae, Kim and Byung-Jo, Ha, supra). This is a cause to make the cross sectional area of the surfactant small. Some of the POE vitamin E in which the hydrophilic moiety polyoxyethylene (POE) chain is short, i.e., the POE vitamin E of small sizes, is too well adsorbed into the skin owing to the instability of the short POE chain and the excellent surface activity. Thus, there is demanded an improvement in compatibility with the skin. In detail, where the POE chain alone is short, it is likely to degrade. Additionally, because the hydrophobic, flat, hard chromane ring moiety, which serves as a mesogen in the formation of liquid crystals, aligns one by one neatly while the phytyl tail has fluidity, the POE vitamin E is too readily inserted into the lipid bilayers of cell membranes, causing a problem in safe use on the skin. This safety problem may be overcome by controlling the length of the ethylene oxide chain of the surfactant, that is, by extending the ethylene oxide chain. In this case, however, the POE vitamin E is too hydrophilic to maintain predetermined HLB values, thereby a desirable surfactant function cannot be obtained.

In order to avoid the safety problem of the POE vitamin E which is superior in high surface activity, but low in the polymerization degree of EO, the present inventors performed various experiments. In one of the experiments, the structure of POE vitamin E was altered in such a way that the hydrophobic POP was joined to a terminal portion of the hydrophilic POE to produce POP-POE vitamin E in which the hydrophilic POE chain is interposed between two hydrophobic moieties, with the expectation that, the amphiphile would have an appropriate size ratio between hydrophobic and hydrophilic regions and thus could form vesicles like diacyl phospholipids which form liposomes with closed bilayer membranes. In addition to being superior in surface activity, the POP-POE vitamin E was found to have excellent ability to form liquid crystal membranes similar to biomembranes and be safe for use on the skin, as disclosed in Korean Pat. Appl'n No. 10-1998-20750. Despite these advantages, the POP-POE vitamin E does not afford the production of stable emulsion products with low viscosity which hardly undergo separation.

DISCLOSURE OF THE INVENTION

Leading to the present invention, the intensive and thorough research into the physiological activity and structural orientation of vitamin E, resulted in the finding that surfactant molecules are improved in biocompatibility by increasing their size and sectional areas, and in their surfactant activity by lengthening their POE chains.

In non-ionic surfactants with POE chains, the sectional area of the effective hydrophilic head increases with increasing of the ethoxylation degree of POE. Since a longer POE chain, when added to a hydrophobic moiety, has a larger sectional area, a surfactant with a longer POE chain is absorbed into the skin to a lesser extent, and is therefore more improved in stability (Surfactant Aggregation, P24, J. H. Glint, Chapman & Hall, New York, 1992). As for polymers of EO and PO, their short chains are problematic in terms of bio-safety because short chains of EO and PO are more easily dissociated than long chains. Block copolymers of PO and EO are very low in toxicity level and their toxicity and irritancy decrease with increasing of molecular weight (Encyclopedia of Polymer Science and Engineering, 2nd Ed. 1986, Vol. 6, p265, John Wiley & Sons U.S.A.). It is already known that non-ionic surfactants are safer to the body as their POE chains are longer.

With the background of the invention in mind, the present inventors have conducted further research into improving the safety of surfactants having long POE chains while maintaining its high surface activity and finally found that, if a long hydrophobic moiety is added to a long hydrophilic moiety, the resulting compound has a controlled ratio of hydrophilic group to hydrophobic group and is safe to the body without modulation in the predetermined HLB value.

In this regard, the hydrophobic moiety to be introduced must meet the requirement for easy synthesis, compatibility with the skin, and economic benefit. After extensive experiments with various candidates, POP was determined as the most suitable moiety because it is relatively flexible owing to the methyl side chain and can provide proper hydrophobicity for vitamin E. In the present invention, POP is bonded to the hard, flat chromane ring of vitamin E to increase hydrophobicity, thereby bringing about the effect of reducing the critical micelle concentration. The surfactant of the present invention can be applied to emulsion products of low viscosity as well as general emulsion products, solubilization products, and dispersion products.

Therefore, it is an object of the present invention to provide a novel modified vitamin E which exhibits high surface activity and safety for use on the skin.

It is another object of the present invention to provide a novel modified vitamin E which is useful in cosmetics, foods, and medicines.

It is a further object of the present invention to provide a method for preparing such a novel modified vitamin E.

It is still a further object of the present invention to provide uses of such a novel modified vitamin E in skin care, drug delivery and surface modification.

In accordance with an aspect of the present invention, there is provided novel POE-POP vitamin E, represented by the following general formula I:

wherein, wherein m is an integer of 1 to 250;

$R_2$ is —$(OCH_2CH_2)_n$— wherein n is an integer of 1 to 250;

B is —$CH_3$ at the 5-, 7- or 8-position of vitamin E; and p is an integer of 1 to 3.

In accordance with another aspect of the present invention, there is provided a method for preparing the novel POE-POP vitamin E, represented by the following formula I, in which the vitamin E represented by the following general formula II is subjected to addition with PO, represented by the following formula III, in the presence of a catalyst and then, with EO, represented by the following formula IV, in the presence of a catalyst:

[I]

[II]

[III]

[IV]

wherein, wherein m is an integer of 1 to 250;

$R_2$ is —$(OCH_2CH_2)_n$— wherein n is an integer of 1 to 250;

B is —$CH_3$ at the 5-, 7- or 8-position of vitamin E; and p is an integer of 1 to 3.

In accordance with a further aspect of the present invention, there are provided a skin care agent, a drug delivery system, or a surface modifier, which all contain the novel POE-POP vitamin E.

In the present invention, the POE-POP vitamin E is prepared by addition-polymerization of PO to the hydroxy group (OH) of natural or synthetic vitamin E to give POP vitamin E which is then subjected to polyethoxylation at high temperature under anhydrous conditions in the presence of a Lewis acid catalyst or an alkaline catalyst. The POE-POP vitamin E thus obtained is tested for whether it functions well as a surfactant, an anti-oxidant and a skin care agent without harmful effects on the body. In this regard, it is evaluated for anti-oxidation activity by measuring its peroxide value, for foaming ability and foam stability by dynamic foam testing, and for surface tension by the du Nuoy method. As for the safety to the human body, it is confirmed through eye irritation tests and patch tests.

BRIEF DESCRIPTION OF THE DRAWINGS

The above and other objects, features and other advantages of the present invention will be more clearly understood from the following detailed description taken in conjunction with the accompanying drawings, in which.

BEST MODES FOR CARRYING OUT THE INVENTION

In the present invention, novel POE-POP vitamin E is prepared by the sequential addition of vitamin E with propylene oxide and ethylene oxide in the presence of an alkaline or Lewis acidic catalyst.

First, synthetic vitamin E is reacted with PO in the presence of methoxy sodium ($CH_3ONa$) to give POP vitamin E which is then reacted with EO in the presence of the same catalyst to POE-POP vitamin E which is in a liquid phase at room temperature. This POE-POP vitamin E is analyzed for properties.

In another embodiment, the same polypropoxylation and polyethoxylation is conducted using different amounts of synthetic vitamin E, PO and EO and different kinds of catalysts, to give POE-POP vitamin E which is in a liquid phase at room temperature.

In a further embodiment, a synthetic vitamin E is subjected to polypropoxylation and then polyethoxylation in the presence of methoxy sodium using different amounts of vitamin E, PO, EO and catalyst, to give POE-POP vitamin E which is in a semi-solid phase at room temperature.

In still a further embodiment, synthetic vitamin E is reacted with PO in the presence of KOH to give POP vitamin E which is then reacted with EO in the presence of KOH to give POE-POP vitamin E which is in a solid phase at room temperature.

In still another embodiment, synthetic vitamin E is reacted with PO in the presence of KOH to give POP vitamin E which is then reacted with EO in the presence of KOH to give POE-POP vitamin E which is in a liquid phase at room temperature.

In still another embodiment, natural vitamin E is reacted with PO in the presence of KOH to give POP vitamin E which is then reacted with EO in the presence of KOH to give POE-POP vitamin E which is in a solid phase at room temperature.

In still another embodiment, natural vitamin E is reacted with PO in the presence of KOH to give POP vitamin E which is then reacted with EO in the presence of KOH to give POE-POP vitamin E which is in a liquid phase at room temperature.

In still another embodiment, vitamin E is reacted with PO in the presence of KOH to give POP vitamin E which is then reacted with EO in the presence of KOH to give POE-POP vitamin E which is in a semi-solid phase at room temperature.

In still another embodiment, natural vitamin E is reacted with PO in the presence of boron fluoride to give POP vitamin E which is then reacted with EO in the presence of boron fluoride to give POE-POP vitamin E which is in a solid phase at room temperature.

The novel POE-POP vitamin E is tested for anti-oxidation activity. In this regard, POE-POP vitamin E is added to linoleic acid and its peroxide value change is analyzed with the lapse of time. Also, the foaming ability and foam stability of the surfactant is measured according to dynamic foam testing. The du Nuoy method is used to measure the surface tension of the surfactant. The surfactants of the present invention are applied to emulsion products of low viscosity and dispersion products. In this regard, emulsion products of low viscosity prepared made up of the surfactant are measured for stability at high temperature (40° C.). A measurement is also made of the stability of dispersion products of the novel POE-POP vitamin E. The safety to the human body is confirmed through eye irritation tests and patch tests.

When preparing the POE-POP vitamin E, account must be taken of vitamin E's being a secondary alcohol with anti-oxidation activity, which is a characteristic of phenol. Another consideration is that the reactive hydroxy group of vitamin E is slowly reacted in an early reaction stage owing to the steric hindrance of neighboring $CH_3$ groups. Accordingly, the quantity of the alkaline or acidic catalyst and the reaction temperature and pressure to be used must be carefully determined.

As the starting material, vitamin E may be a synthetic one, such as dl α-tocopherol, dl β-tocopherol, dl γ-tocopherol, or dl δ-tocopherol, a natural one, such as that extracted from plant seeds, or vitamin E ester, such as vitamin E acetate, vitamin E succinate or vitamin E lactate.

Useful examples of the alkaline catalysts include $CH_3ONa$, NaOH and KOH while the Lewis acid catalyst may be selected from $BF_3$, $SnCl_4$ and $SbCl_5$. Based on the weight of the starting material or the POE vitamin E, the catalysts each are used at an amount of 0.02 to 0.8% by weight, but the amount may be changed depending on reaction conditions.

The addition reaction is generally carried out at a temperature of 110 to 185° C. and preferably 145 to 160° C. under a pressure of 0.9 to 9.0 $kg/cm^3$ and preferably 3.5 to 6.0 $kg/cm^2$.

A better understanding of the present invention may be obtained in the light of the following examples which are set forth to illustrate, but are not to be construed to limit the present invention.

EXAMPLE 1

Preparation of POE(20 EO)-POP(10 PO) Vitamin E (1)

In a 2 L double stainless steel autoclave were introduced 125 g (0.29 mol) of synthetic vitamin E (dl α-tocopherol) and then, 0.15 g of highly pure methoxy sodium ($CH_3ONa$). The reactor was demoisturized by heating to 78° C. under vacuum of about 750 mmHg for about 30 min. Thereafter, 170 g (2.93 mol) of PO was added to the reactor under pressure and allowed to react at 155–160° C. for about 7 hours, so as to give a liquid phase of POP vitamin E. After being further added with 0.1 g of methoxy sodium, the liquid was subjected to addition reaction with 265 g (6.02 mol) of EO over a period of 7 hours at 160–165° C. with stirring.

After completion of the reaction, the reactor was purged three times with gaseous nitrogen to remove unreacted PO and EO and the by-product 1,4-dioxane. The reaction mixture was cooled to about 50° C., followed by adding a trace amount of citric acid to neutralize the alkaline catalyst. After unreacted vitamin E was extracted with toluene, the product was purified by column chromatography on Sephadex LH-50, eluting with a chloroform-methanol (1:1, v/v), to afford 543.2 g of POE(20 EO)-POP(10 PO) vitamin E(1) in a highly viscous liquid phase. The highly viscous liquid product was analyzed as follows.

Figure 1:
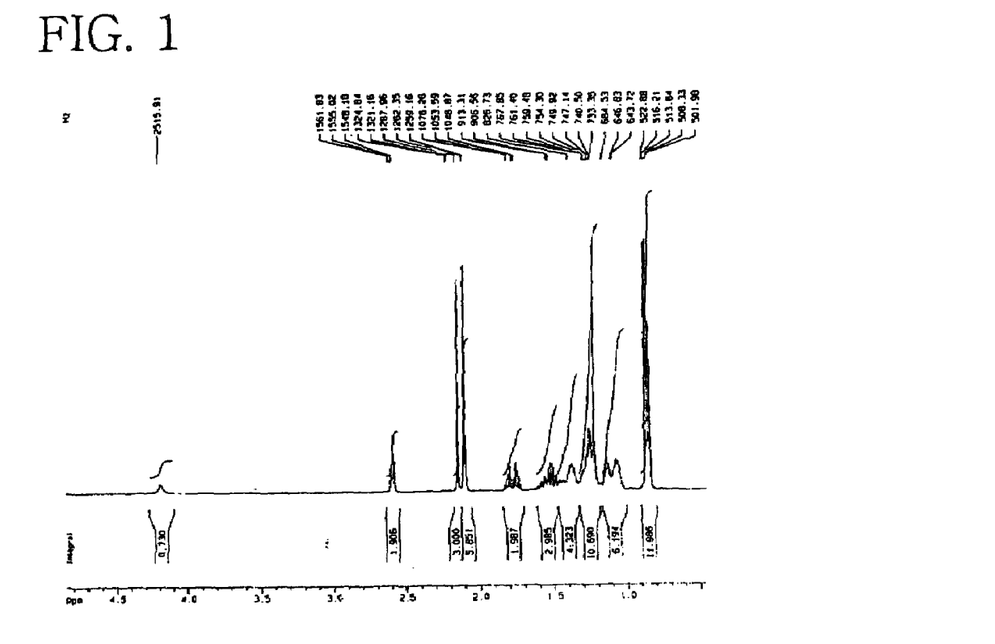
FIG. 1 is an $^1$H-NMR spectrum of synthetic vitamin E (dl α-tocopherol)
Figure 2:
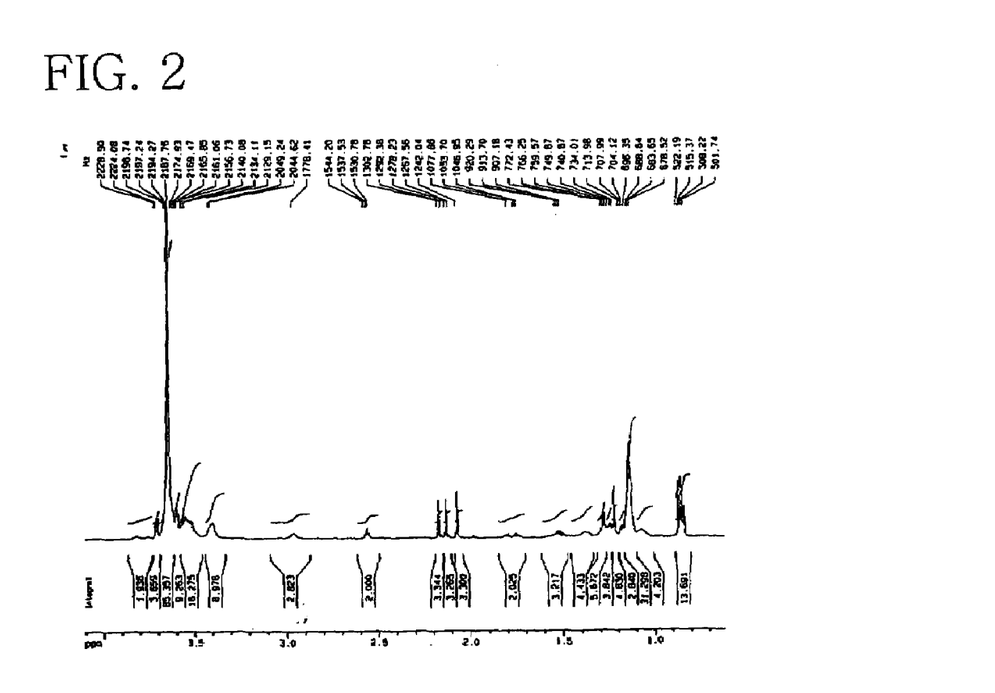
FIG. 2 is an $^1$H-NMR spectrum of the POE(20EO)-POP (10PO) vitamin E (1) prepared in Example 1.

Analysis Results
(1) Appearance: a pale yellow liquid at room temperature
(2) Elemental Analysis: as a relative molecular weight of $C_{99}H_{190}O_{32}$
Calculated (%): C, 62.86; H, 10.05; N, 0.00
Found (%): C, 63.62; H, 10.80; N, 0.03
(3) Yield: 97.0%
(4) Moles of Added PO: 10 moles on average
(5) Moles of Added EO: 20 moles on average
(6) NMR spectrum $^1$H-NMR spectra for the synthetic vitamin E and the POE-POP vitamin E(1) are shown in FIGS. 1 and 2, respectively. As seen, the NMR spectrum of FIG. 1 has a peak for —$CH_3$ read at 0.8–0.9 δ, a peak for —$CH_2CH_2$— at 1.17–1.35 δ, three peaks for the —$CH_3$ of the phenyl group at 2.05–2.15 δ, and a peak for the —OH group of the trimethyl phenol at 4.15 δ. In the NMR spectrum of FIG. 2, the peak for —OH at 4.15 δ disappears while peaks for the H of PEO —$(CH_2CH_2O)_m$— and for the H of the —(CH—$CH_2$—O)$_n$— of PPO —$(CH(CH_3)$—$CH_2$—O)$_n$H appear at 3.55–3.75 δ. Also, an H peak of the terminal —OH of the PPO appears at 3.85 δ and a peak for the —$CH_3$ of polypropylene oxide —$(CH(CH_3)$—$CH_2$—O)$_n$— is additionally detected at 1.2–1.6 δ.

EXAMPLE 2

Preparation of POE(5 EO)-POP(20 PO) Vitamin E (2)

In a 2 L double stainless steel autoclave were introduced 125 g (0.29 mol) of synthetic vitamin E (dl α-tocopherol) and then, 0.1 g of highly pure potassium hydroxide (99.9%). The reactor was demoisturized by heating to 76° C. under vacuum of about 755 mmHg for about 30 min. Thereafter, 345 g (5.95 mol) of PO was added to the reactor under pressure and allowed to react at 160–165° C. for about 6 hours with stirring, so as to give a liquid phase of POP vitamin E. After being further added with 0.08 g of potassium hydroxide (99.9%), the liquid was subjected to addition reaction with 65 g (1.48 mol) of EO over a period of 8 hours at 165–170° C. to afford POE-POP vitamin as yellow liquid.

After completion of the reaction, the reactor was purged three times with gaseous nitrogen to remove unreacted PO and EO and the by-product 1,4-dioxane. The reaction mixture was cooled to about 60° C., followed by adding a trace amount of hydrochloric acid to neutralize the alkaline catalyst. After unreacted vitamin E was extracted with toluene, the product was purified by column chromatography on Sephadex LH-50, eluting with a chloroform-ethanol (7:3), to afford 520.0 g of POE-POP vitamin E(2) in a liquid phase. The highly viscous liquid product was analyzed as follows.

Figure 3:
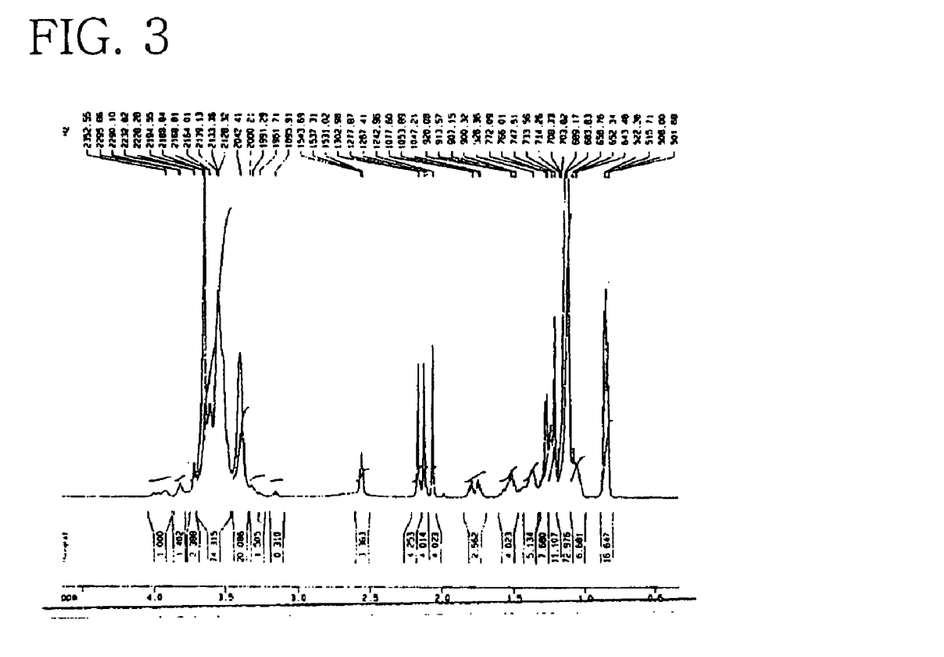
FIG. 3 is an $^1$H-NMR spectrum of the POE(5EO)-POP (20PO) vitamin E (2) prepared in Example 2.

Analysis Results
(1) Appearance: a pale yellow liquid at room temperature
(2) Elemental Analysis: as a relative molecular weight of $C_{99}H_{145}O_{27}$
Calculated (%): C, 67.31; H, 12.21; N, 0.00
Found (%): C, 66.97; H, 12.12; N, 0.03
(3) Yield: 97.2%
(4) Moles of Added PO: 20 moles on average
(5) Moles of Added EO: 5 moles on average
(6) NMR spectrum As seen, the NMR spectrum of FIG. 1 has a peak for —$H_3$ read at 0.8–0.9 δ, a peak for —$CH_2CH_2$— at 1.17–1.35 δ, three peaks for the —$CH_3$ of the phenyl group at 2.05–2.15 δ, and a peak for the —OH group of the trimethyl phenol at 4.15 δ. An $^1$H-NMR spectrum for the POE-POP vitamin E(2) obtained in Example 2 is shown in FIG. 3. In the NMR spectrum of FIG. 3, when being compared with the NMR spectrum of FIG. 1, the peak for —OH at 4.15 δ disappears while peaks for the H of PEO —$(CH_2CH_2O)_m$— and for the H of the —$(CH-CH_2-O)_n$— of PPO —$(CH(CH_3)-CH_2-O)_n$H appear at 3.55–3.75 δ. Also, an H peak of the terminal —OH of the PPO appears at 3.85 δ and a peak for the —$CH_3$ of polypropylene oxide —$(CH(CH_3)-CH_2-O)_n$— is additionally detected at 1.2–1.3 δ.

The spectrum of FIG. 3 is similar in pattern to, but higher than, that of FIG. 2 because the moles of the PO used in this Example were greater than that used in Example 1.

EXAMPLE 3

Preparation of POE(30EO)-POP(20PO) Vitamin E (3)

In a 2L double stainless steel autoclave were introduced 112 g (0.26 mol) of synthetic vitamin E (dl α-tocopherol) and then, 0.12 g of highly pure methoxy sodium. The moisture inside the reactor was removed by heating to 76° C. under vacuum of about 750 mmHg for about 30 min. Thereafter, 310 g (5.34 mol) of PO was added to the reactor under pressure and allowed to react at 160–165° C. for about 6 hours with stirring, so as to give a liquid phase of POP vitamin E. This liquid was subjected to addition reaction with 350 g (7.95 mol) of EO over a period of 8 hours at 160–165° C. in the presence of 0.10 g of methoxy sodium to give a yellow liquid phase.

After completion of the reaction, the reactor was purged three times with gaseous nitrogen to remove unreacted PO and EO and the by-product 1,4-dioxane. The reaction mixture was cooled to about 60° C., followed by adding a trace amount of hydrochloric acid to neutralize the alkaline catalyst. After unreacted vitamin E was removed with toluene, the reaction was purified by column chromatography on Sephadex LH-50, eluting with a chloroform-ethanol (1:1, v/v), to afford 754 g of POE-POP vitamin E(3) in a semi-liquid phase. The semi-liquid phase product was analyzed as follows.

Figure 4:
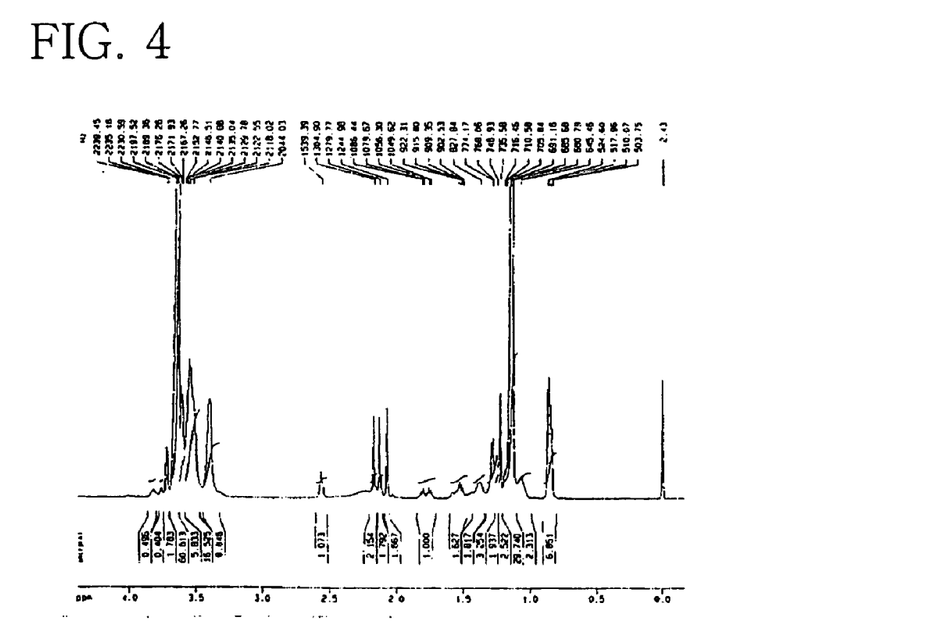
FIG. 4 is an $^1$H-NMR spectrum of the POE(30EO)-POP (20PO) vitamin E (3) prepared in Example 3.

Analysis Results
(1) Appearance: a pale yellow semi-solid phase at room temperature
(2) Elemental Analysis: as a relative molecular weight of $C_{149}H_{290}O_{52}$
Calculated (%): C, 61.44; H, 9.97; N, 0.00
Found (%): C, 62.05; H, 10.52; N, 0.03
(3) Yield: 97.7%
(4) Moles of Added PO: 20 moles on average
(5) Moles of Added EO: 30 moles on average
(6) NMR spectrum As seen, the NMR spectrum of FIG. 1 has a peak for —$H_3$ read at 0.8–0.9 δ, a peak for —$CH_2CH_2$— at 1.17–1.35 δ, three peaks for the —$CH_3$ of the phenyl group at 2.05–2.15 δ, and a peak for the —OH group of the trimethyl phenol at 4.15 δ. An $^1$H-NMR spectrum for the POE-POP vitamin E(3) obtained in Example 3 is shown in FIG. 4. In this NMR spectrum, when being compared with the NMR spectrum of FIG. 1, the peak for —OH at 4.15 δ disappears while peaks for the H of PEO —$(CH_2CH_2O)_m$— and for the H of the —$(CH-CH_2-O)_n$— of PPO —$(CH(CH_3)-CH_2-O)_n$H appear at 3.55–3.75 δ. Also, an H peak of the terminal —OH of the PPO appears at 3.85 δ and a peak for the —$CH_3$ of PPO —$(CH(CH_3)-CH_2-O)_n$— is additionally detected at 1.2–1.3 δ. The spectrum of FIG. 4 is similar in pattern to, but taller than that of FIG. 2 because the moles of the POE and PPO used in this Example were greater than those used in Example 1.

EXAMPLE 4

Preparation of POE(50 EO)-POP(20 EO) Vitamin E (4)

In a 2 L double stainless steel autoclave were introduced 125 g (0.29 mol) of synthetic vitamin E (dl α-tocopherol) and then, 0.10 g of highly pure potassium hydroxide (99.9%). The reactor was demoisturized by heating to 75° C. under vacuum of about 750 mmHg for about 30 min. Thereafter, 350 g (6.03 mol) of PO was added to the reactor under pressure and allowed to react at 160–165° C. for about 6 hours with stirring, so as to give a liquid phase of POP vitamin E. After being further added with 0.13 g of potassium hydroxide (99.9%), the liquid was subjected to addition reaction with 650 g (14.8 mol) of EO over a period of 8 hours at 160–165° C. to afford POE-POP vitamin as yellow solid.

After completion of the reaction, the reactor was purged three times with gaseous nitrogen to remove unreacted PO and EO and the by-product 1,4-dioxane. The reaction mixture was cooled to about 70° C., followed by adding a trace amount of hydrochloric acid to neutralize the alkaline catalyst. After unreacted vitamin E was extracted with toluene, the product was purified by column chromatography on Sephadex LH-50, eluting with a chloroform-ethanol (2:3), to afford 1071 g of POE-POP vitamin E(4) in a solid phase. The solid product was analyzed as follows.

Analysis Results
(1) Appearance: a pale yellow solid at room temperature
(2) Elemental Analysis: as a relative molecular weight of $C_{189}H_{370}O_{72}$
Calculated (%): C, 59.84; H, 9.76; N, 0.00
Found (%): C, 60.05; H, 10.12; N, 0.03
(3) Yield: 95.2%

Figure 5:
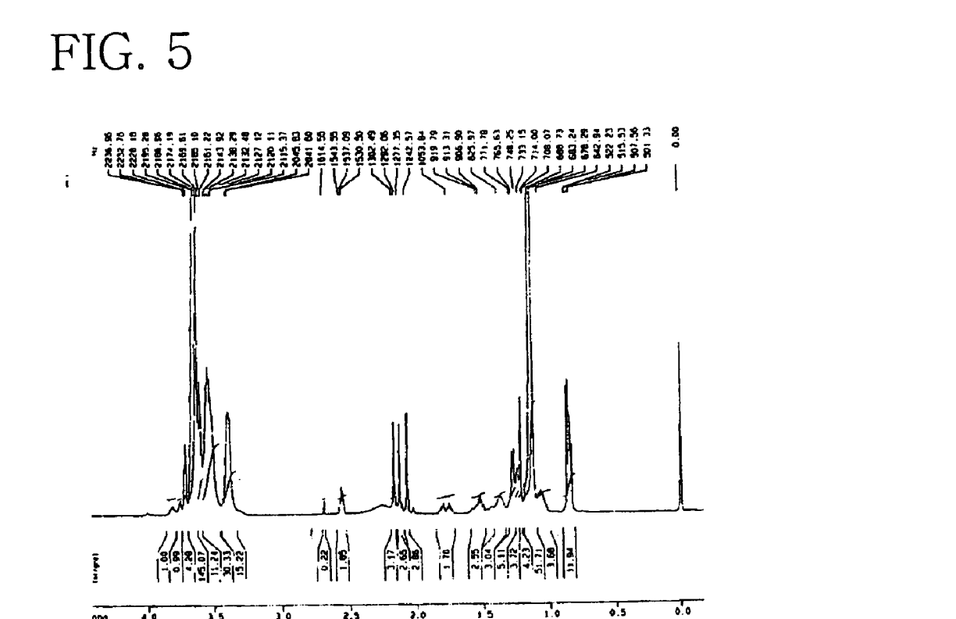
FIG. 5 is an $^1$H-NMR spectrum of the POE(50EO)-POP (20PO) vitamin E (4) prepared in Example 4.

(4) Moles of Added PO: 20 moles on average
(5) Moles of Added EO: 50 moles on average
(6) NMR spectrum As seen, the NMR spectrum of FIG. 1 has a peak for —CH$_3$ read at 0.8–0.9 δ, a peak for —CH$_2$CH$_2$— at 1.17–1.35 δ, three peaks for the —CH$_3$ of the phenyl group at 2.05–2.15 δ, and a peak for the —OH group of the trimethyl phenol at 4.15 δ. An $^1$H-NMR spectrum for the POE-POP vitamin E(4) obtained in Example 4 is shown in FIG. 5. In the NMR spectrum of FIG. 5, when being compared with the NMR spectrum of FIG. 1, the peak for —OH at 4.15 δ disappears while peaks for the H of PEO —(CH$_2$CH$_2$O)$_m$— and for the H of the —(CH—CH$_2$—O)$_n$— of PPO —(CH(CH$_3$)—CH$_2$—O)$_n$H appear at 3.55–3.75 δ. Also, an H peak of the terminal —OH of the PPO appears at 3.85 δ and a peak for the —CH$_3$ of polypropylene oxide —(CH(CH$_3$)—CH$_2$—O)$_n$— is additionally detected at 1.2–1.6 δ.

The spectrum of FIG. 5 is similar in pattern to, but higher than, that of FIG. 2 because the moles of the PO and EO used in this Example were greater than those used in Example 1.

EXAMPLE 5

Preparation of POE(70 EO)-POP(50 PO) Vitamin E (5)

In a 2 L double stainless steel autoclave were introduced 56 g (0.13 mol) of synthetic vitamin E (dl α-tocopherol) and then, 0.15 g of highly pure potassium hydroxide (99.9%). The reactor was demoisturized by heating to 82° C. under vacuum of about 755 mmHg for about 40 min. Thereafter, 390 g (6.72 mol) of PO was added to the reactor under pressure and allowed to react at 160–165° C. for about 8 hours with stirring, so as to give a liquid phase of POP vitamin E. In the presence of 0.15 g of potassium hydroxide (99.9%), the liquid was subjected to addition reaction with 420 g (9.55 mol) of EO over a period of 8 hours at 165–170° C. to afford POE-POP vitamin as yellow solid.

After completion of the reaction, the reactor was purged three times with gaseous nitrogen to remove unreacted PO and EO and the by-product 1,4-dioxane. The reaction mixture was cooled to about 70° C., followed by adding a trace amount of hydrochloric acid to neutralize the alkaline catalyst. After unreacted vitamin E was extracted with toluene, the product was purified by column chromatography on Sephadex LH-50, eluting with chloroform-ethanol (5:4), to afford 829.6 g of POE-POP vitamin E(5) in a liquid phase. The liquid product was analyzed as follows.

Figure 6:
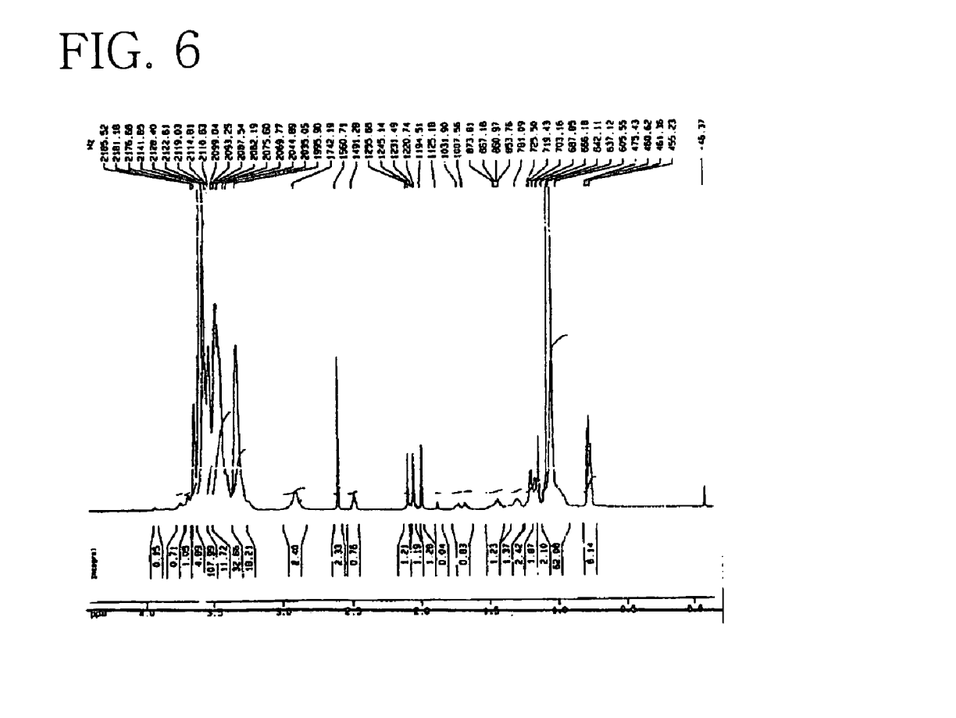
FIG. 6 is an $^1$H-NMR spectrum of the POE(70EO)-POP (50PO) vitamin E (5) prepared in Example 5.

Analysis Results
(1) Appearance: a pale yellow liquid at room temperature
(2) Elemental Analysis: as a relative molecular weight of C$_{319}$H$_{630}$O$_{122}$
  Calculated (%): C, 59.72; H, 9.83; N, 0.00
  Found (%): C, 60.25; H, 9.88; N, 0.05
(3) Yield: 95.8%
(4) Moles of Added PO: 50 moles on average
(5) Moles of Added EO: 70 moles on average
(6) NMR spectrum As seen, the NMR spectrum of FIG. 1 has a peak for —H$_3$ read at 0.8–0.9 δ, a peak for —CH$_2$CH$_2$— at 1.17–1.35 δ, three peaks for the —CH$_3$ of the phenyl group at 2.05–2.15 δ, and a peak for the —OH group of the trimethyl phenol at 4.15 δ. An $^1$H-NMR spectrum for the POE-POP vitamin E(5) obtained in Example 5 is shown in FIG. 6. In the NMR spectrum of FIG. 6, when being compared with the NMR spectrum of FIG. 1, the peak for —OH at 4.15 δ disappears while peaks for the H of PEO —(CH$_2$CH$_2$O)$_m$— and for the H of the —(CH—CH$_2$—O)$_n$— of PPO —(CH(CH$_3$)—CH$_2$—O)$_n$H appear at 3.55–3.75 δ. Also, an H peak of the terminal —OH of the PPO appears at 3.85 δ and a peak for the —CH$_3$ of polypropylene oxide —(CH(CH$_3$)—CH$_2$—O)$_n$— is additionally detected at 1.2–1.6 δ.

The spectrum of FIG. 6 is similar in pattern to, but higher than, that of FIG. 2 because the moles of the PO and EO used in this Example was greater than those used in Example 1.

EXAMPLE 6

Preparation of POE(70 EO)-POP(100 PO) Vitamin E(6)

In a 2L double stainless steel autoclave were introduced 56 g (0.13 mol) of natural vitamin E (α, β, γ, and δ-tocopherol mixture) and then, 0.17 g of highly pure potassium hydroxide (99.9%). The moisture inside the reactor was removed by heating to 75° C. under vacuum of about 755 mmHg for about 50 min. Thereafter, 775 g (13.36 mol) of PO was added to the reactor under pressure and allowed to react at 150–160° C. for about 8 hours with stirring, so as to give a liquid phase of POP vitamin E. The liquid was subjected to addition reaction with 425 g (9.6 mol) of EO over a period of 8 hours at 160–165° C. in the presence of 0.15 g of potassium hydroxide (99.9%) to give a yellow solid phase.

After completion of the reaction, the reactor was purged three times with gaseous nitrogen to remove unreacted PO and EO and the by-product 1,4-dioxane. The reaction mixture was cooled to about 80° C., followed by adding a trace amount of hydrochloric acid to neutralize the alkaline catalyst. After unreacted vitamin E was removed with toluene, the reaction was purified by column chromatography on Sephadex LH-50, eluting with chloroform-methanol (2:3), to afford 1186 g of POE-POP vitamin E(6) in a solid phase. The solid product was analyzed as follows.

Figure 7:
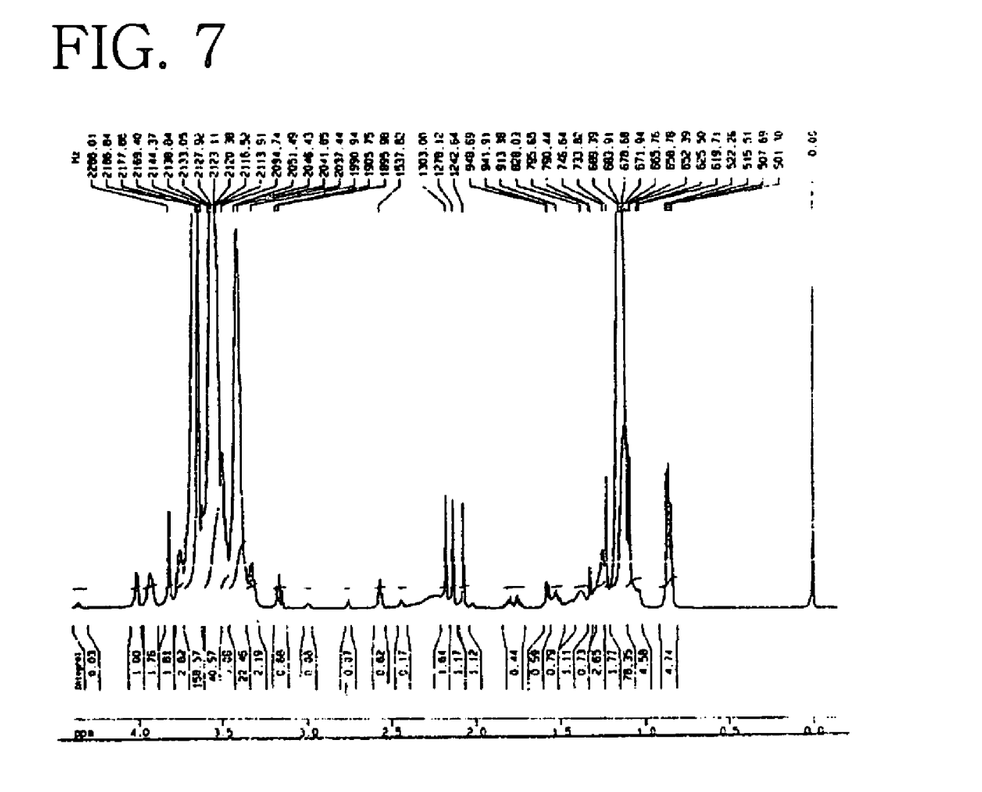
FIG. 7 is an $^1$H-NMR spectrum of the POE(70EO)-POP (100PO) vitamin E (6) prepared in Example 6.

Analysis Results
(1) Appearance: a pale yellow solid phase at room temperature
(2) Elemental Analysis: as a relative molecular weight of C$_{469}$H$_{930}$O$_{172}$
  Calculated (%): C, 60.45; H, 9.90; N, 0.00
  Found (%): C, 61.05; H, 10.12; N, 0.06
(3) Yield: 94.5%
(4) Moles of Added PO: 100 moles on average
(5) Moles of Added EO: 70 moles on average
(6) NMR spectrum As seen, the NMR spectrum of FIG. 1 has a peak for —CH$_3$ read at 0.8–0.9 δ, a peak for —CH$_2$CH$_2$— at 1.17–1.35 δ, three peaks for the —CH$_3$ of the phenyl group at 2.05–2.15 δ, and a peak for the —OH group of the trimethyl phenol at 4.15 δ. An $^1$H-NMR spectrum for the POE-POP vitamin E(6) obtained in Example 6 is shown in FIG. 7. In the NMR spectrum of FIG. 7, when being compared with the NMR spectrum of FIG. 1, the peak for —OH at 4.15 δ disappears while peaks for the H of PEO —(CH$_2$CH$_2$O)$_m$— and for the H of the —(CH—CH$_2$—1)$_n$— of PPO —(CH(CH$_3$)—CH$_2$—O)$_n$H appear at 3.55–3.75 δ. Also, an H peak of the terminal —OH of the PPO appears at 3.85 δ and a peak for the —CH$_3$ of polypropylene oxide —(CH(CH$_3$)—CH$_2$—O)$_n$— is additionally detected at 1.2–1.6 δ.

The spectrum of FIG. 7 is similar in pattern to, but higher than, that of FIG. 6 because the moles of the PO used in this Example was greater than those used in Example 5.

EXAMPLE 7

Preparation of POE(5 EO)-POP(20 PO) Vitamin E (7)

The same procedure as in Example 2 was repeated with modification of using 116 g (0.29 mol) of natural vitamin E (α, β, γ, and 6-tocopherol mixture) instead of synthetic vitamin E, to produce 509 g of POE-POP vitamin E (7) (20 PO moles and 5 EO moles on average).

EXAMPLE 8

Preparation of POE(50 EO)-POP(20 PO) Vitamin E (8)

The same procedure as in Example 4 was repeated with modification of using 134 g (0.29 mol) of vitamin E acetate instead of synthetic vitamin E, to afford 1138 g of POE-POP vitamin E (8) (20 PO moles and 50 EO moles on average) as a semi-solid phase.

EXAMPLE 9

Preparation of POE(70 EO)-POP(100 PO) Vitamin E (9)

The same procedure as in Example 4 was repeated with modification of using 54.3 g (0.13 mol) of natural vitamin E (α, β, γ, and δ-tocopherol mixture) instead of synthetic vitamin E in the presence of $BF_3$ instead of potassium hydroxide, to afford 1150 g of POE-POP vitamin E (9) (100 PO moles and 70 EO moles on average) as a solid pahse.

EXAMPLE 10

Anti-Oxidation Activity of POE-POP Vitamin E

The novel POE-POP vitamin E of the present invention was examined for anti-oxidation activity, using linoleic acid. Readily being oxidized, linoleic acid can be used in determining the ability of an antioxidant of interest to inhibit the oxidation of linoleic acid. Used in this test was reagent-grade linoleic acid that comprised linoleic acid 85% and linolenic acid 15%.

POE-POP vitamin E prepared in Example 1, 2 or 3 was added in an amount of 0.5% to linoleic acid while vitamin E, vitamin E acetate, POE (12EO) vitamin E, POE (24 EO)-cholesterol, POE (20 EO) sorbitan monostearate, and POE (12 EO) nonylphenylether were also used as references. These samples were stored in an incubator maintained at 40° C. After two and ten days of incubation, a peroxide value was determined for each sample. In detail, in 1.0 g of each sample was placed in a 250 ml Erlenmeyer flask and dissolved with 10 ml of chloroform. To the solution, 15 ml of glacial acetic acid and 1 ml of saturated potassium iodide solution were added, and a stopper was put in the flask. After being vigorously shaken, the flask was allowed to stand in a dark place for 5 min. Thereafter, the flask was added with 75 ml of distilled water and vigorously shaken. Free iodine was titrated with a 0.01 N sodium thiosulfate solution, using a starch solution as an indicator. The point at which the solution became colorless was regarded as the end point. The peroxide value was calculated as follows:

$$POV(meq/kg) = \frac{(S-B) \times F}{\text{Amount of Sample (g)}}$$

wherein,

S: Amount of 0.01 N sodium thiosulfate solution consumed by sample (ml)

B: Amount of 0.01 N sodium thiosulfate solution consumed in blank test tube (ml)

F: Factor of 0.01 N sodium thiosulfate solution

The results are summarized in Table 1, below. It is apparent from the data of Table 1 that the POE-POP vitamin E (1), (2) and (3) prepared in Examples 1, 2 and 3, respectively, although less potent in anti-oxidation activity than the physiologically active antioxidant vitamin E, show similar anti-oxidation activity to that of vitamin E acetate and POE (12 EO) vitamin E, with superiority over POE (24EO) cholesterol and POE (12 EO) nonylphenylether.

TABLE 1

Peroxide Values

| Samples | Day 2 | Day 10 |
|---|---|---|
| 1. Linoleic Acid (5° C.) | 15.7 | 16.8 |
| 2. Linoleic Acid (40° C.) | 30.6 | 167.2 |
| 3. Linoleic acid + Vitamin E (0.5%) | 21.6 | 58.9 |
| 4. Linoleic acid + Vitamin E acetate | 26.2 | 122.3 |
| 5. Linoleic acid + POE (20 EO)-POP (10 PO) Vitamin E (1) (0.5%) | 24.9 | 118.6 |
| 6. Linoleic acid + POE (5 EO)-POP (20 PO) Vitamin E (2) (0.5%) | 26.3 | 121.8 |
| 7. Linoleic acid + POE (30 EO)-POP (20 PO) Vitamin E (3) (0.5%) | 26.9 | 120.4 |
| 8. Linoleic acid + POE (24 EO) Cholesterol (0.5%) | 27.8 | 169.4 |
| 9. Linoleic acid + POE (12 EO) Vitamin E (0.5%) | 26.0 | 121.6 |
| 10. Linoleic acid + POE (20 EO) sorbitan mono stearate (0.5%) | 25.9 | 133.6 |
| 11. Linoleic acid + POE (12 EO) nonylphenylether (0.5%) | 28.9 | 178.5 |

EXAMPLE 11

Surface Activity of POE-POP Vitamin E

In order to examine the surface activity of the novel POE-POP vitamin E of the present invention, the POE-POP vitamin E prepared in the examples was tested for surface tension, foaming ability and foam stability, along with other control surfactants.

Experiment 1: Foaming Ability and Foam Stability

Foaming ability, one of the representative properties of surfactants, is a good test item. The foaming ability and foam stability were determined according to a dynamic foam test. In a 2 L scaled cylinder with an inner diameter of 10 cm was charged 400 cc of a 0.1% solution of each sample in water and the solution was stirred at 1,000 rpm at 20° C. for 1 min with an agimixer. The height of the foam layer thus formed was regarded as foaming ability while the foam stability was expressed by the volume of the foam layer formed immediately after the stirring as a percentage of the same maintained at three minutes after the stirring. The results are given in Table 2, below.

Comparison of foaming ability and foam stability between POE (20 EO)-POP (10 PO) vitamin E (1) of Example 1 and a corresponding POE (18 EO) vitamin E revealed the influence of the added hydrophobic moiety POP (10 PO). As seen, the hydrophobic moiety brought a great reduction in foaming ability and foam stability, which reflects that the added POP has a great influence on the strength of the hydrophobic moiety of POE-POP vitamin E. However, the increased strength of the hydrophobic moiety can be compensated by an increase in hydrophilicity, i.e., by adding a long POE chain to obtain a balanced HLB value as demonstrated with POE (50EO)-POP (20PO) vitamin E (4) of Example 4. Also, the data of Table 2 demonstrate that the POE-POP vitamin E (5) with 10 moles of PO and 50 moles of EO on average is higher in foaming ability and foam stability than the POE-POP vitamin E (1), POE-POP vitamin E (3) and POE (24 EO) cholesterol, and shows almost the same foaming ability and foam stability as the POE (40EO) vitamin E used as a reference.

TABLE 2

Foaming Ability and Foam Stability

| Samples | Foaming Ability (cc) | Foam Stability (%) |
|---|---|---|
| 1. POE (24 EO) Cholesterol | 246 | 89.6 |
| 2. POE (40 EO) Vitamin E | 262 | 88.5 |
| 3. POE (18 EO) Vitamin E | 255 | 87.6 |
| 4. POE (20 EO)-POP (10 PO) Vitamin E (1) | 185 | 46.5 |
| 5. POE (20 EO)-POP (20 EO) Vitamin E (3) | 212 | 74.6 |
| 6. POE (50 EO)-POP (20 PO) Vitamin E (4) | 257 | 91.2 |

Experiment 2: Surface Tension

At 25° C., 0.1% solutions of samples in water were measured for surface tension according to the du Nuoy method with the aid of a surface tension balance manufactured by Fisher Scientific. The results are given in Table 3, below. As shown in Table 3, the POE(50EO)-POP(20PO) vitamin E (4) of Example 4 has a surface tension of 41.0 dyne/cm, slightly lower than that of POE (24EO) cholesterol or POE(30EO) vitamin E. Thus, POE-POP vitamin E of the present invention was proven to be a better surfactant.

TABLE 3

Surface Tension in 0.1% Aqueous Solution (20° C.)

| Samples | Surface Tension (dyne/cm) |
|---|---|
| 1. POE (24 EO) cholesterol | 48.4 |
| 2. POE (18 EO) vitamin E | 42.1 |
| 3. POE (40 EO) vitamin E | 45.4 |
| 4. POE (30 EO)-POP (20 PO) Vitamin E (3) | 45.7 |
| 5. POE (50 EO)-POP (20 PO) Vitamin E (4) | 41.0 |
| 6. POE (70 EO)-POP (50 PO) Vitamin E (5) | 48.5 |

Experiment 3: Stability of Oil-in-Water Type Emulsion Product of Low Viscosity

Emulsifying capacity is one of the most important properties of surfactants and is primarily dependent on the HLB of the material. In consideration of the fact that emulsifying capacity and emulsion stability are affected by various factors such as surfactant structure, this experiment employed very simple oil-in-water emulsion systems dependent utterly on surfactants only, each consisting of 60% of liquid paraffin as an oil phase, 5% of a surfactant, and water as an aqueous phase, in testing for emulsion stability. Because the HLB required for O/W emulsion of liquid paraffin is 6, preliminary experiments were made at around this HLB value to determine that emulsion systems with HLB values somewhat higher than 6 are more stable. Based on the pre-test data, the POE-POP vitamin E surfactants of the present invention were tested, together with various surfactants, including combinations of the typical hydrophilic surfactant POE(20 EO) sorbitant stearate (ICI Surfactants U.S.A.) and the typical lipophilic surfactant sorbitan cesquiolate (ICI Surfactants U.S.A.), and POE vitamin E, for stability. In this regard, emulsion systems were emulsified with the aid of a homogenizer at 70° C. at 1,000 rpm for 5 min and cooled to 40° C., followed by incubation at 40° C. Emulsion stability was expressed by the height of the stable layer as a percentage of the total layer 1 and 20 days after incubation. The results are given in Table 4, below.

Figure 8:
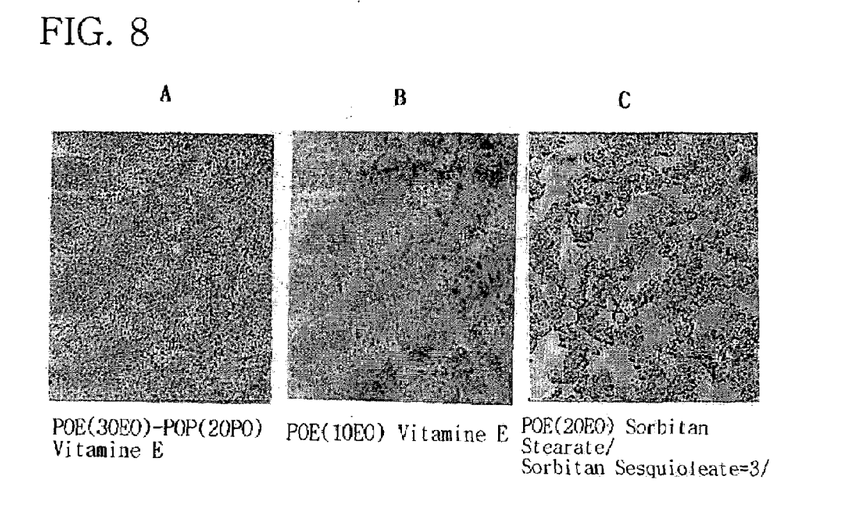
FIG. 8 is microphotographs showing low viscosity O/W products emulsified with the POE(30EO)-POP(20PO) vitamin E (3) of Example 3 and control emulsifiers after 20 days of incubation at 40° C.

As apparent in data of Table 4, POE-POP vitamin E prepared in Examples 1 and 3 is superior in emulsion stability to the control emulsifiers used. Of the controls, POE(10 EO) vitamin E shows excellent apparent stability against phase segregation, like the surfactants of the present invention, owing to its structural characteristics. However, POE (10 EO) vitamin E, although showing no indication of apparent segregation, as seen in FIG. 8, was inferior to the surfactants of the present invention in particle size distribution. This reflected that POE (10 EO) vitamin E underwent particle aggregation or agglomeration at high temperatures. Additionally, as afore-mentioned, relatively short POE chains joined to vitamin E have such small molecular sectional areas as to penetrate into the skin with ease, causing, for example, skin irritation. In the present invention, POP is used, in combination with POE, to increase the hydrophobicity with maintenance of the same HLB value as with POE alone, thereby producing more stable surfactants which allow the production of low viscosity emulsion products with high safety for use in the skin. Addition of POE to POP vitamin E was found to bring about higher stability against decomposition than other hydroxy groups such as those of fatty alcohols, due to the effect of high molecular weight even when the adduct is low in molecular weight. Thus, the O/W emulsion products of low viscosity made of the POE-POP vitamin E could be improved in stability against decomposition in addition to safety for use on the skin.

TABLE 4

Emulsion Stability of O/W Emulsion Products of Low Viscosity

| | | Stability % at 40° C. | |
|---|---|---|---|
| Surfactant | wt % | Day 1 | Day 20 |
| 1. POE (20 EO) sorbitan stearate/sorbitan cesquiolate = 3/1 | 5 | 75 | 53 |
| 2. POE (20 EO) sorbitan stearate/sorbitan cesquiolate = 3/2 | | 81 | 48 |
| 3. POE (20 EO) sorbitan stearate/sorbitan cesquiolate = 2/3 | | 78 | 39 |
| 4. POE (8 EO) vitamin E | | 78 | 81 |
| 5. POE (10 EO) vitamin E | | 100 | 92 |
| 6. POE (18 EO) vitamin E | | 88 | 75 |
| 7. POE (20 EO)-POP (10 PO) vitamin E (1) | | 100 | 98 |
| 8. POE (30 EO)-POP (20 PO) vitamin E (3) | | 100 | 97 |

Experiment 4: Stability of Water-in-Oil Type Emulsion Product of Low Viscosity

Unlike oil-in-water type emulsion, water-in-oil type emulsion has oil as a continuous phase and is difficult to stabilize by electrostatic processes. For industrial use, water-in-oil type emulsion is stabilized by minimizing the surfactant layer adsorbed to the interface, the viscosity of dispersant, and/or the difference of specific gravity between dispersion medium and dispersed phase. In most cases, the problem of stabilizing water-in-oil type emulsions is solved with highly viscous products. It is very difficult to stabilize water-in-oil products of low viscosity at high temperatures and in fact, there have been reported rare successes in the industrial development of such products.

In this experiment, water-in-oil emulsion products of low viscosity were tested for stability in the same manner as in Experiment 3. The results are summarized in Table 5, below. As apparent from data of Table 5, POE (5 EO)—POP (20 PO) vitamin E (2) prepared in Example 2 shows excellent W/O emulsion stability, compared to control emulsifiers in current commercial use. Representative of W/O surfactants in current industrial use, sorbitan cesquiolate could not stabilizer emulsions under the experimental conditions of requiring the accomplishment of the stabilization only by the surface activity of surfactants themselves. POE (5 EO) vitamin E exhibited considerable stability, but yet still inferior to POE-POP vitamin (2) of Example 2.

Figure 9:
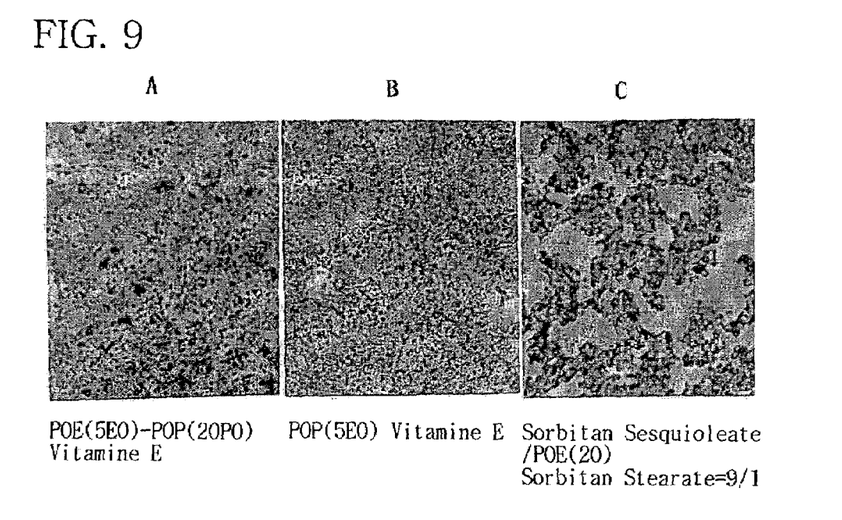
FIG. 9 is microphotographs showing low viscosity W/O products emulsified with the POE(50EO)-POP(20PO) vitamin E (2) of Example 2 and control emulsifiers after 20 days of incubation at 40° C.

With reference to FIG. 9, there are shown microphotographs of W/O emulsion products obtained after 20 days of storage in an incubator at 40° C. As in the observation with the naked eye, the POE-POP vitamin E (2) of Example 2 was proven excellent in stability, compared to the control surfactants, by microscopic observation.

Through this experiment, it is understood that vitamin E alone is not sufficient to achieve desired stability and that, after the enrichment of hydrophobicity through the addition of POP, POE addition brings excellent stability to the W/O surfactant. As described for the hydrophilic surfactant, the lipophilic POE vitamin E having a relatively small POE head joined to vitamin E can easily penetrate into the skin owing to its small molecular sectional area, irritating the skin. In the present invention, the addition of the hydrophobic moiety POP increases the molecular size and the subsequent addition of POE enlarges the molecular sectional area. Furthermore, the POE, even if small in size, becomes resistant to decomposition by virtue of the POP moiety bonded thereto. Therefore, the resulting surfactant is improved in stability, enabling the production of W/O emulsion products of low viscosity, which are stable and safe for use on the skin.

TABLE 5

Emulsion Stability of W/O Emulsion Products of Low Viscosity

| | | Stability % at 40° C. | |
|---|---|---|---|
| Surfactant | wt % | Day 1 | Day 20 |
| 1. sorbitan cesquiolate/ POE (20 EO) sorbitan stearate = 10/0 | 5 | 75 | 43 |
| 2. sorbitan cesquiolate/ POE (20 EO) sorbitan stearate = 9/1 | | 65 | 52 |
| 3. sorbitan cesquiolate/ POE (20 EO) sorbitan stearate = 8/2 | | 78 | 46 |
| 4. POE (3 EO) vitamin E | | 58 | 55 |
| 5. POE (5 EO) vitamin E | | 100 | 70 |
| 6. POE (5 EO)-POP (20 PO) vitamin E (2) | | 100 | 98 |

Experiment 5: Dispersion Stability of Dispersion Product

The dispersion stability of the products containing pigment or insoluble solids is very important. As in the test for emulsion stability, this experiment employed dispersion systems consisting of 2.5% of dispersive surfactant, 5% of pigment, 10% of liquid paraffin oil, 0.5% of cetostearyl alcohol, and the remainder of deionized water, in order to evaluate the performance dependence on dispersing agents, with as complete exclusion of other factors as possible.

As in the test for emulsion stability, dispersion systems were dispersed by heating at 70° C. and cooled to 40° C., followed by incubation at 40° C. Dispersion stability was expressed by the height of the stable layer as a percentage of the total layer 1 and 20 days after incubation. The results are given in Table 6, below.

Compared to the control surfactants, as apparent in data of Table 6, POE-POP vitamin E (4) and (5) prepared in Examples 4 and 5 exhibited higher dispersion stability. Of the controls, POE(10 EO) vitamin E are also of excellent apparent dispersion stability, like the surfactants of the present invention, owing to its structural characteristics. Taken together, the data obtained in this experiment demonstrate that POE-POP vitamin E obtained according to the present invention are economically favorable surfactants and allow the development of dispersion products improved in quality and stability.

TABLE 6

Dispersion Stability

| | | Stability % at 40° C. | |
|---|---|---|---|
| Surfactant | wt % | Day 1 | Day 10 |
| 1. POE (20 EO) sorbitan stearate/ sorbitan cesquiolate = 4/1 | 5 | 85 | 78 |
| 2. POE (20 EO) sorbitan stearate/ sorbitan cesquiolate = 3/1 | | 78 | 75 |
| 3. POE (18 EO) vitamin E | | 93 | 92 |
| 4. POE (30 EO) vitamin E | | 76 | 67 |
| 5. POE (50 EO)-POP (20 PO) vitamin E (4) | | 99 | 96 |
| 6. POE (70 EO)-POP (50 PO) vitamin E (5) | | 95 | 94 |

EXAMPLE 12

Safety in Living Body

1. Eye Irritation Test

To evaluate the safety of the novel POE-POP vitamin E, an eye irritation test was conducted on 10 healthy rabbits (body weight 2.8 kg on average) as taught by Draize. The POE-POP vitamin E (1), (2) and (4) prepared respectively in Examples 1, 2 and 4, POE (12EO) vitamin E, POE (12EO) nonylphenylether (Nikko Japan), and POE (20EO) sorbitan monostearate each were diluted with a 10% aqueous glycerine solution to give a 10% sample solution. This test sample was dropped onto one eye of each rabbit while the other eye was used as a control. 24 hours later, the average scores were recorded according to the Draize scoring for ocular lesions. If lesions were present, the time was extended; otherwise, observation was ceased.

The results are summarized in Table 7, below. As seen in Table 7, the POE(20EO)-POP(10PO) vitamin E (1) of Example 1, the POE(5EO)-POP(20PO) vitamin E (2) of Example 2, and the POE(50EO)-POP(20PO) vitamin E (4) of Example 4 are weaker irritants than the other test samples, that is, POE(10EO) vitamin E, POE(18EO) vitamin E, POE(50EO), POE(20EO) sorbitan monostearate, and POE (12EO) nonylphenylether and therefore, can be used safely in medicines, foods, and cosmetics, such as elemental cosmetics, make-up cosmetics and hair-care cosmetics. The addition amount of the POE-POP vitamin E according to the present invention is dependent on its purposes and the kinds of the materials it is to be used together with, but preferably on the order of approximately 0.05 to 60% by weight.

TABLE 7

Eye Irritation Test According to Draize Procedure

| Sample | Avg. Value |
|---|---|
| 1. Glycerine (10%) | 0.00 |
| 2. POE (20 EO)-POP (20 PO) Vitamin E (1) | 0.05 |
| 3. POE (5 EO)-POP (20 PO) Vitamin E (2) | 0.10 |
| 4. POE (50 EO)-POP (20 PO) Vitamin E (4) | 0.03 |
| 5. POE (10 EO) Vitamin E | 0.35 |
| 6. POE (18 EO) Vitamin E | 0.25 |
| 7. POE (50 EO) Vitamin E | 0.05 |
| 8. POE (12 EO) nonylphenylether | 0.65 |
| 9. POE (20 EO) sorbitan monostearate | 0.08 |

2. Patch Test

To confirm non-toxicity of the POE-POP vitamin E of Examples 1, 2 and 5, a patch test was conducted on the human body according to the Finn Chamber method. The subjects of this test were 40 females 15–35 years old. A sample material was dropped onto the brachium of each of the subjects and a dermicel tape was bonded thereto. The skin irritations were evaluated as a response rate (%) according to an International Contact Dermatitis Research Group (ICDRG) standard after 24 or 48 hours. The results are given in Table 8, below. The data shown in Table 8 demonstrate the POE-POP vitamin E does not irritate the skin, with safety similar to that of POE(20EO) sorbitan monostearate, and is safer to apply to the skin than the controls, POE(12EO) vitamin E and POE (12EO) nonylphenyl ether.

TABLE 8

Patch Test

| Samples | Response Rate (%) | |
|---|---|---|
| | 24 h | 48 h |
| 1. POE (20 EO)-POP (10 PO) Vitamin E (1) | 0.5 | 0.0 |
| 2. POE (5 EO)-POP (20 PO) Vitamin E (2) | 0.3 | 0.0 |
| 3. POE (70 EO)-POP (50 PO) Vitamin E (5) | 0.3 | 0.0 |
| 4. POE (20 EO) sorbitan monostearate | 0.6 | 0.0 |
| 5. POE (12 EO) Vitamin E | 0.8 | 0.6 |
| 6. POE (12 EO) nonylphenylether | 1.7 | 1.4 |

INDUSTRIAL APPLICABILITY

The POE-POP vitamin E of the present invention, as described hereinbefore, can be prepared by the two-step addition reaction of the antioxidant and physiologically active vitamin E with PO and then with EO in the proper ratio, and is of high surface activity and safe for use on the skin with skin soothing and antioxidant functions. In the POE-POP vitamin E, the POP serves as a hydrophobic moiety to compensate for the insufficient hydrophobicity of vitamin E alone, while the POE acts as a hydrophilic head. Thus, the POE-POP vitamin E can bear a longer hydrophilic head than can POE vitamin E at the same HLB value. Additionally, EO moieties of a long POE chain are more resistant to decomposition than those of a short POE chains.

Furthermore, the POE-POP vitamin E of the present invention has high anti-oxidation activity and is economically favorable, compared with POE vitamin E. The large molecular cross sectional area of the POE-POP vitamin E makes it difficult for the molecule to penetrate into the skin. Therefore, it is very safe to apply to the skin. In addition to exhibiting excellent surface activity in emulsions, solutions and dispersions under general conditions, the surfactant of the present invention is highly stable in O/W or W/O emulsion products of very low viscosity. Consequently, the present invention can be very advantageously used in the cosmetic, food, medicine industries and other surface science technology-applied industries.

The present invention has been described in an illustrative manner, and it is to be understood the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

The invention claimed is:

1. A polyoxyethylene-polyoxypropylene vitamin E, of chemical formula wherein

$R_2$ comprises wherein m is an integer of 1 to 250;

$R_1$ comprises $H(OCH_2CH_2)_n$-, wherein n is an integer of 1 to 250;

A is or

B is —$CH_3$ at the 5-, 7- or 8-position of vitamin E; and p is an integer of 1 to 3.

2. A method for preparing a polyoxyethylenepolyoxypropylene vitamin E of chemical formula wherein $R_2$ comprises wherein m is an integer of 1 to 250; $R_1$ comprises $H(OCH_2CH_2)_n$, wherein n is an integer of 1 to 250; A is or

;

B is —$CH_3$ at the 5-, 7- or 8-position of vitamin E; and p is an integer of 1 to 3; wherein the vitamin E comprises synthetic or natural vitamin E of chemical formula or a vitamin E ester comprising an acetate, succinate or lactate of vitamin E, wherein A, B and p are as defined above, is subjected to an addition reaction with propylene oxide of chemical formula in the presence of a catalyst, and then with ethylene oxide of chemical formula in the presence of a catalyst.

3. The method as ser forth in claim 2, wherein the synthetic vitamin E comprises d1-α tocopherol, d1-β tocopherol, d1-γ tocopherol or d1-δ tocopherol.

4. The method as set forth in claim 2, wherein in the polyoxyethylne-polypropylene vitamin E m and n are 1 to 250 and 1 to 250, respectively, and having suitable surface activity.

5. The method as set forth in claim 2, wherein the addition reaction in the presence of the catalyst is carried out at a pressure of 0.8- to 9.0 kg/cm$^2$.

6. The method as set forth in claim 2, wherein the catalyst is present in an amount of 0.02 to 0.8% by weight in the polypropoxylation step and the polyethoxylation step, respectively, and is an alkaline catalyst comprising $CH_3ONa$, NaOH or KOH or a Lewis acid catalyst comprising $BF_3$, $SnCl_4$ or $SbCl_5$.

7. The method as set forth in claim 2, wherein the addition reaction is carried out at a temperature of 110 to 185° C.

8. A composition comprising the polyoxyethylene-polyoxypropylene vitamin E of claim 1, and a carrier or diluent.

* * * * *

UNITED STATES PATENT AND TRADEMARK OFFICE
CERTIFICATE OF CORRECTION

PATENT NO. : 7,144,919 B1  
APPLICATION NO. : 10/362160  
DATED : December 5, 2006  
INVENTOR(S) : Kim et al.

Page 1 of 1

It is certified that error appears in the above-identified patent and that said Letters Patent is hereby corrected as shown below:

Claim 3, Column 22, Line 22,  
Please delete "ser" and  
replace with -- set --

Signed and Sealed this

Sixth Day of February, 2007

JON W. DUDAS  
*Director of the United States Patent and Trademark Office*